(12) United States Patent
Sykes (10) Patent No.: US 6,237,422 B1
(45) Date of Patent: May 29, 2001

(54) APPARATUS AND METHOD FOR TESTING STRENGTH OF ELECTRICAL BOND SITES ON SEMICONDUCTOR DEVICES

(75) Inventor: Robert Sykes, Tendring (GB)

(73) Assignee: Dage Precision Industries Ltd. (GB)

( * ) Notice: Subject to any disclaimer, the term of this patent is extended or adjusted under 35 U.S.C. 154(b) by 0 days.

(21) Appl. No.: 09/208,165

(22) Filed: Dec. 9, 1998

(30) Foreign Application Priority Data

Dec. 13, 1997 (GB) ................................................. 9726355
Feb. 10, 1998 (GB) ................................................. 9802674
May 19, 1998 (GB) ................................................. 9810650

(51) Int. Cl.⁷ ....................................................... G01N 3/02
(52) U.S. Cl. ................................................ 73/859; 73/827
(58) Field of Search ........................... 73/826, 827, 833, 73/835, 842, 856, 859, 860, 150 A (56) References Cited

U.S. PATENT DOCUMENTS

| 2,141,284 | * | 12/1938 | Woock | 73/859 |
| 3,170,322 | * | 2/1965 | Cavanaugh | 73/859 |
| 4,662,229 | * | 5/1987 | Curtis | 73/859 |
| 5,054,324 | * | 10/1991 | Pohl | 73/859 |
| 5,056,372 | * | 10/1991 | Estano | 73/859 |

* cited by examiner

Primary Examiner—Max Noori
(74) Attorney, Agent, or Firm—Kilpatrick Stockton LLP (57) ABSTRACT

A test device for applying a tensile force to electrical bond sites of a semiconductor device includes jaws (21), adapted to closely engage the surface of the bond site, typically a solder ball (22), while an inner edge portion (23) of each jaw approaches the jaw axis. By closely confining the bond site, the clamping forces exerted can be increased without risk that the bond site will be crushed. In a preferred embodiment the jaws permit slight reshaping of the bond site to increase the area of engagement therewith.

10 Claims, 7 Drawing Sheets

APPARATUS AND METHOD FOR TESTING STRENGTH OF ELECTRICAL BOND SITES ON SEMICONDUCTOR DEVICES

This invention concerns a device and method for testing the integrity of a bond between an electrical device and an electrical conductor thereof.

Electrical semiconductor devices are very small. Typically a silicon wafer or chip comprising an electrical circuit is encapsulated in or affixed to a relatively rigid substrate; the substrate is necessary in order to give the wafer sufficient mechanical strength. Several silicon devices may be attached to a single substrate.

Individual semiconductor device comprising a number of silicon chips are usually fixed with other electrical components to a printed circuit board in order to make a complete control device, for example for a personal computer.

A typical prior art semiconductor device has peripheral connection sites whereby edge contacts can be connected to a circuit board or to an intermediate circuit assembly. Usually these connection sites are densely packed in a linear array around the semiconductor device. Electrical connections are by way of individual wires bonded to the semiconductor connection site at one end, and to the circuit board at the other end.

Reductions in size of the semiconductor device, due to advances in technology, have resulted in insufficient edge length for the necessary number of connection sites. Accordingly the connection sites may be arranged in a rectangular array over the face of the device. This requires a new method of making electrical connections, and it has been proposed to provide raised bumps of electrically conductive material at each connection site. In order to make connection to another component, such as a circuit board, the bumps are placed in register over a corresponding array of connection sites, and the bumps are bonded in order to form a permanent electrical connection. In the case of bumps of solder, the solder is reflowed in order to make the connection. In the case of bumps of gold, pressure may be sufficient to form a good bond. Other methods may also be suitable, and the bumps may be formed of other materials.

Such bumps are typically in the size range 0.05–1.0 mm in diameter, and a single control device may incorporate many hundreds of bumps of a similar shape and size.

Test methods are required in order to have confidence that the bumps are adequately bonded to the connection sites prior to connection to the corresponding connection sites; for example by solder reflow. Typically a shear test is used whereby a test head pushes the bump sideways to measure the breakaway force. Continual testing is required in order to identify statistical trends which indicate deviation from the desired quality standard.

A problem arises in the case of multi-layer substrates having a plurality of electrical printed circuits separated by intermediate insulating layers. Such substrate are also a result of miniaturization whereby sufficient electrical tracks cannot be provided in a single layer. Typically the outer layer of substrate will have apertures to permit electrical connection to the internal electrical tracks, and the bumps are thus partially within the printed circuit substrate instead of being wholly on the surface thereof.

The same problem can arise where an electrical track on the surface of the substrate has a solder bump bond site defined by a solder resist mask, which may for example be screen printed on the substrate. The mask confines the solder as it is applied to the substrate, and has the effect of raising the surface of the substrate with respect to the bond site.

Clearly a shear test is inappropriate for these kinds of partially buried bump since the wall of the aperture in the outer layer of substrate will support the bump and thus resist shear forces. Accordingly a tensile test is required.

It has been proposed to apply a test head to a solder bump, heat the head to reflow the solder whereby the bump and test head are bonded, and apply a tensile force after the bond has cooled. This has the disadvantage of being slow, requiring a new test head for each test, and of potentially affecting the bond site itself as the solder is reflowed to attach the test head. This later disadvantage is an especial problem since the arrangement of metal layers at the base of the bump may be complex, and the application of heat may affect the metallurgy thereof.

Other proposals have included gripping the bump between jaws. In the case of plain jaws the difficulty is to develop sufficient friction whilst avoiding crushing loads. Since the bump is often approximately hemispherical, the jaws typically make a point contact, and thus the local stress on the bump can be very high; this solution has proved impractical.

Another solution provides pointed jaws to indent the bump so as to improve traction, but in practice the bump is likely to shear at the plane of the jaws due to inward migration of the opposed indents. Furthermore, both of the mechanical gripping proposals may change the shape of the bump sufficiently to reduce confidence that the electrical bond breaks only as a result of the tensile test.

According to the present invention there is provided a test head of a device for tensile testing electrically conductive projections of an electrical device, the test head having jaws closable on a projection thereby to grip the projection, and adapted to apply a tensile load in the direction of projection thereof, wherein the jaws are adapted to closely engage the projection over a substantial part of the surface thereof, the distal edge portion of each jaw approaching the axis of the jaws.

Typical projections are of solder, gold or a suitable electrically conductive composite material.

Preferably the jaws are concave and substantially part spherical when intended for engagement with a projection such as an arcuate bump of solder. Alternatively the jaws may define a somewhat planar contact surface for bumps which are substantially rectangular.

In a preferred embodiment the jaws confine the bump sufficiently closely to obviate spreading or crushing of the bump under clamping forces. Thus the opposed jaws both clamp and support the bump such that the compressive clamping loads are resisted. The jaws may nevertheless not wholly confine the bump so long as the unconfined portions are not subjected to significant spreading or crushing loads.

In a preferred embodiment the jaws are concave and adapted to engage a bump over greater than 40% of the jaw surface area thereof, preferably over 60%, and most preferably over 75%. In the case of bumps of regular shape, at least 85% and preferably greater than 90% of the jaw surface area is adapted to engage the bump. The jaws may define a relief volume less than 10% of the surface of the bump intended to be gripped by the jaws, and most preferably less than 5% in the case of bumps of regular shape.

In the preferred embodiment the inner edges of the jaws, in the closed condition, are substantially further apart than the width of the electrical contact area of the bump.

Preferably two, three or at most four jaws are provided in order to minimize manufacturing cost.

In a preferred embodiment the jaws may engage the bump sufficiently closely to cause re-shaping forces whereby the bump can more closely conform to the shape of the jaws. The material of the bump, e.g. solder, is relatively soft and a re-shaping of the surface portion is useful in increasing the contact area, and thus reducing areas of high stress. Necessarily the re-shaping must not result in crushing or spreading loads, but can be determined according to the parameters of the bump to be tested. Relevant factors are size, shape and material specification of the bump.

The jaws may include relieved areas to permit re-shaping in a confined and deliberate manner. In this way the close fit of the jaws can support the bump whilst ensuring that excess or mis-shapen material is accommodated within the jaws in a controlled way.

In a preferred embodiment the jaws define a substantially cylindrical bump engaging cavity having sidewalls extending in the direction of the tensile load to be applied. In this embodiment the jaws include respective continuous inwardly directed lips at the distal ends thereof, and preferably the lips are of regular cross-section having blunt bump engaging tips. The depth of the cylindrical cavity is preferably greater than that of the bump with which the jaws are to be engaged in use, so that the jaw cavity has no upper constraint on the bump. The internal diameter of the cavity is chosen such that the bump can be reshaped to engage a substantial area of the sidewalls, typically over a depth in the range of 80%–120% of the mean diameter of the bond site.

According to another aspect the invention comprises a method of testing electrically conductive projections using the device of the present invention, the method comprising the steps of selecting a test head having jaws corresponding closely to the projection over a substantial part of the surface thereof, clamping the projection in the jaws, and re-shaping a surface portion of the projection so as to conform closely to the shape of the jaws, and applying a tensile load to the test head so as to pull the projection in the direction of projection thereof.

Such a method has the advantage of reducing areas of high stress, due to mis-shapen projections, prior to application of the tensile load.

Other features of the invention will be apparent from the following description of several preferred embodiments shown by way of example only in the accompanying drawings in which:

Figure 1:
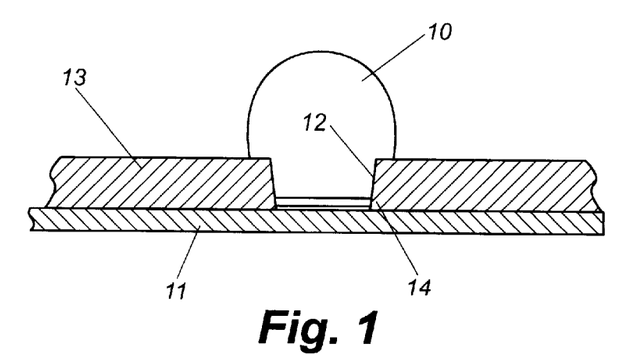
FIG. 1 illustrates a section through a typical solder bump.

FIG. 1 of the drawings illustrates a typical bump 10, of solder, formed on an electrical track 11 within an aperture 12 in an outer layer 13 of insulating material. More electrical tracks and layers of insulating material may be provided. The attachment face of the bump may include several layers 14 of different materials (e.g. Sn, Cu, Au, Ag) in order to improve electrical and mechanical bonding. These additional layers, and the electrical track itself may be formed by masking and electro deposition, and thus be extremely thin; in FIG. 1 the layers shown have considerable thickness for the purposes of illustration.

Figure 2:
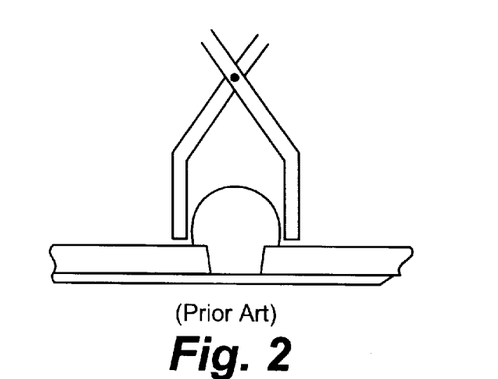
FIGS. 2 and 3 illustrate prior art tensile test methods.
Figure 3:
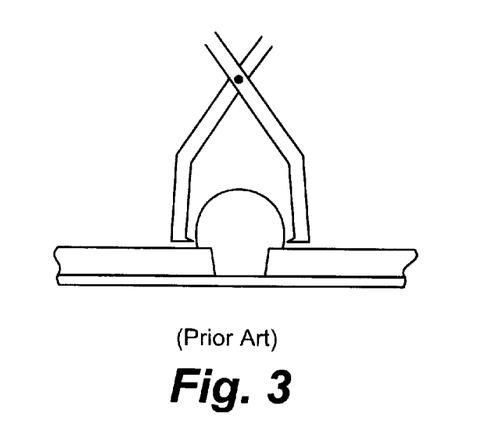

FIG. 2 illustrates the prior art clamp method using plain opposed jaws, and FIG. 3 illustrates the prior art method using pointed jaws. In the case of plain jaws the required clamp force for a tensile test is likely to crush the bump, and in the case of the pointed jaws the bump is likely to shear at the plane of the jaws. Neither prior method gives a reliable indication of the strength of the bond between the bump 10 and the track 11.

Figure 4:
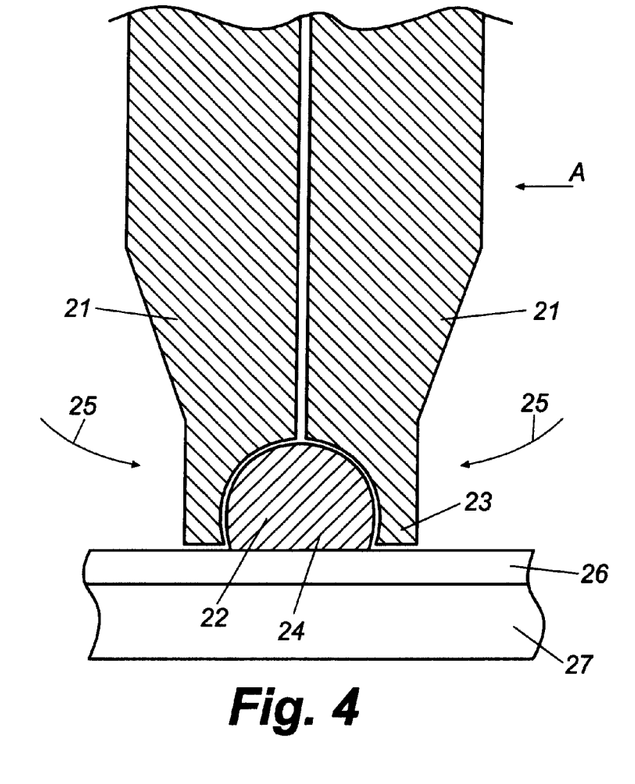
FIG. 4 is a transverse section through a first embodiment of the invention.
Figure 5:
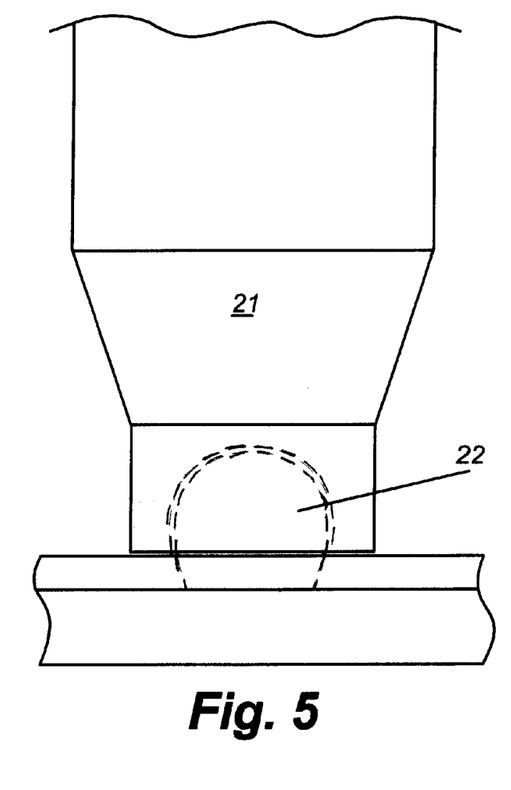
FIG. 5 is an elevation of the first embodiment in the direction of arrow A of FIG. 4.

FIGS. 4 and 5 illustrates one embodiment of the present invention. Opposed jaws 21 substantially encompass the bump 22 over the entire surface area thereof. The jaws include an inwardly directed lower edge 23 for engagement with the naturally somewhat narrower neck portion 24 of the bump. The jaws close in the direction of arrows 25 to clamp the bump 22 and, once gripped, a tensile force is applied in the direction of arrow B. The insulating layer 26 lies over the electrically conductive layer 27 to which the bump 22 is electrically connected, and which defines the plane of the bond to be tested.

An important feature of the invention is that the jaws 21 are arcuate so as to closely conform to the shape of the idealized bump illustrated. This not only increases the surface area of the jaw on the bump, but also reduces the likelihood of the bump spreading or deforming under clamping loads. This latter feature is especially important because significant deformation of the bump may result in fracture sites, or may promote internal cracks and discontinuities which affect the nature of the tensile test to be performed. By substantially supporting the bump in the region of the clamping jaws, such damage is avoided since the bump is trapped in compression by the encompassing nature of the jaw form.

A further advantage of the invention is that by placing the bump under a compressive but supported load, the clamping force can be increased without risk that the bump will be crushed or in extreme cases break up into particles or powder. In fact, since the bump is substantially enclosed, the clamping force can be increased substantially above that at which an unsupported bump would be crushed or otherwise damaged.

The degree to which the bump is subjected to a compressive load by the jaws of the invention is dependent on a number of factors. These include the inherent strength of the solder materials of which the bump is constituted, the approximate shape and size of the bump, the degree of deformation which the bump can withstand without substantially affecting the bond at the electrical track interface and the approximate tensile force to break the bond interface.

For practical reasons of cost and ease of manufacture the jaws are arranged to encompass only sufficient of the bump to give adequate frictional grip without imposing excessive load whilst ensuring that adequate tensile force can be applied to the bond interface. The precise relationship between these factors can be determined by routine tests and are dependent in part on the size and material of the bump, which can vary according to the kind of electrical device being manufactured.

The jaws may closely encompass the bump over the entire exposed surface thereof, or may engage the bump only partially, but sufficiently to exert the required tensile force. For example the gap between the jaws in the closed (clamped) condition may be significant provided that those areas of the bump which are exposed do not result in spreading or other kinds of undesirable weakening of the bump itself. Typically the bump will be clamped over at least 40% of its surface area, though up to 95% clamping may be possible if the bump approaches a regular shape such as a hemisphere, as illustrated in FIGS. 1 and 2.

Figure 6:
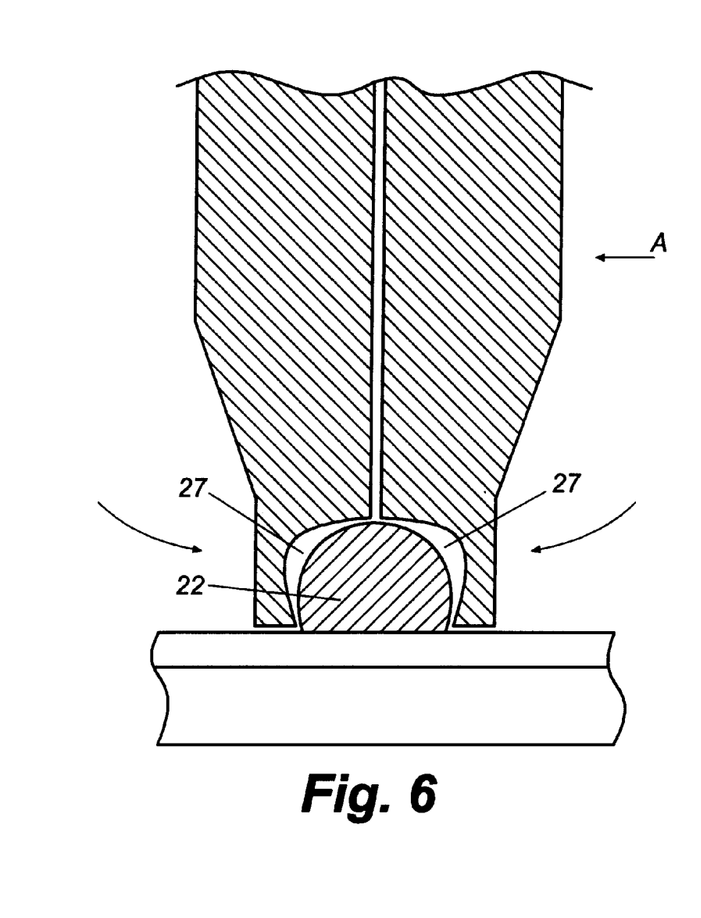
FIG. 6 corresponds to FIG. 4 and shows a second embodiment of the invention.
Figure 7:
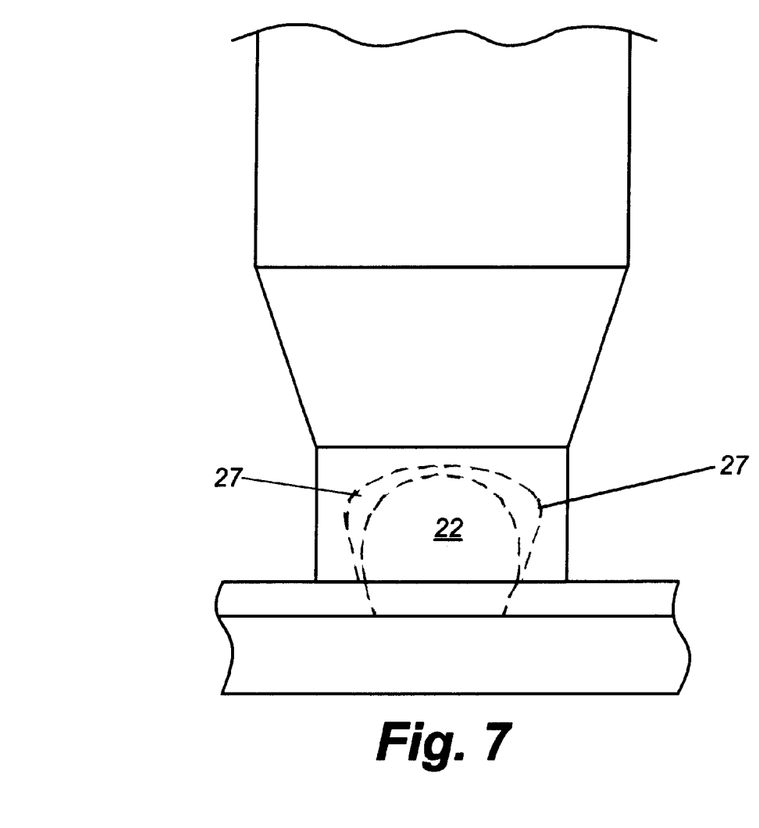
FIG. 7 corresponds to FIG. 5 and shows the second embodiment.

The second embodiment illustrated in FIGS. 6 and 7 corresponds to the first embodiment but has a relief volume 27 to accommodate necessary re-shaping of the bump 22. It will be understood that whilst the bumps are manufactured in millions by a closely controlled process, there will be some bumps that are slightly mis-shapen, and the second embodiment permits re-shaping whilst giving support to the extent necessary. The relief volume shown in FIG. 6 and FIG. 7 is an illustration for example purposes only, and may be smaller or larger, as desired; it may encircle the bump or may be provided only in small areas to permit a degree of local re-shaping, dependent on the typical shape of the bump to be tested. The relief volume, or area of non-contact, is typically on the upper side of the bump where tractive forces need not be applied. It may nevertheless be useful to confuse the upper side of the bump, at least partially, in order to resist compressive loads applied at the lower side.

Figure 8:
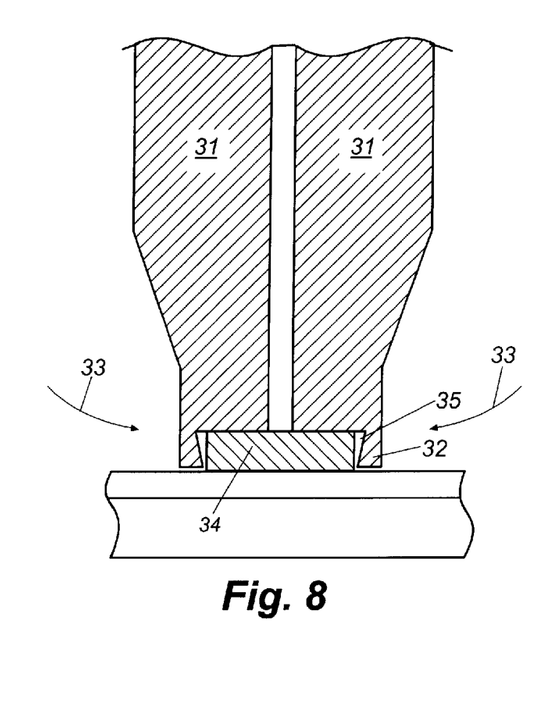
FIGS. 8–10 show a third embodiment, for use in testing rectangular bumps.
Figure 9:
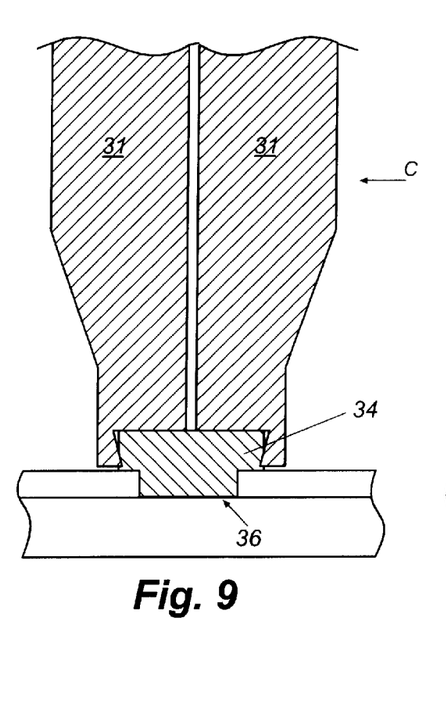

FIGS. 8 and 9 illustrate re-shaping of a rectangular bump in order to apply sufficient clamping force for a successful tensile test.

The jaws 31 are angled inwardly towards the jaw axis at their tips 32. As the jaws close, in the direction of arrows 33, to clamp the rectangular bump 34, the relatively shallow angle of the tips 32 re-shapes the bump, causing swelling into the relief volume 35 at the root of the jaw tips. In this embodiment the shallow angle of the jaw tips, and the close confinement of the bump within the jaws has the effect of preventing migration of any indentation across the plane of the jaws; thus the effect of the prior art arrangement of FIG. 3 is avoided. As illustrated, the upper surface of the rectangular bump 34 is wholly confined in order to resist compressive loads applied to the sides of the bump.

The closed condition of the jaws is illustrated in FIG. 9, which also shows that the area of re-shaping is well outside the area of the bond site 36. This is also the case with the rounded bumps of the first and second embodiments. Typically the area of the bump in the plane of the jaws will be at least 10% greater than the root area to be tested. More typically this area will be 50% or 100% greater than the test area.

Figure 10:
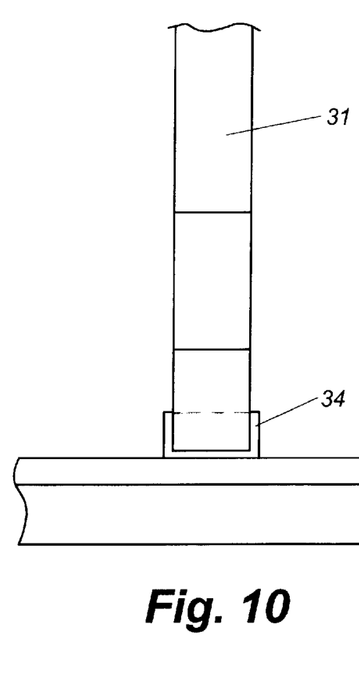

FIG. 10 is an elevation on arrow C of FIG. 9, and shows that the bump is unconfined along two edges. This is possible so long as the bump is sufficiently confined to support compressive loads, and in this example the jaw is in contact with the top edge of the bump, as illustrated. This provides sufficient resistance to prevent sideways spreading. Depending on the parameters of the bump 34, it might be necessary to partially or wholly confine the sides which are exposed in FIG. 10. The bump 34 may for example be confined at the side in the region close to the ends, such that each jaw has a shallow 'U' section in which the side portion is about 50% of the width of the base.

Figure 11:
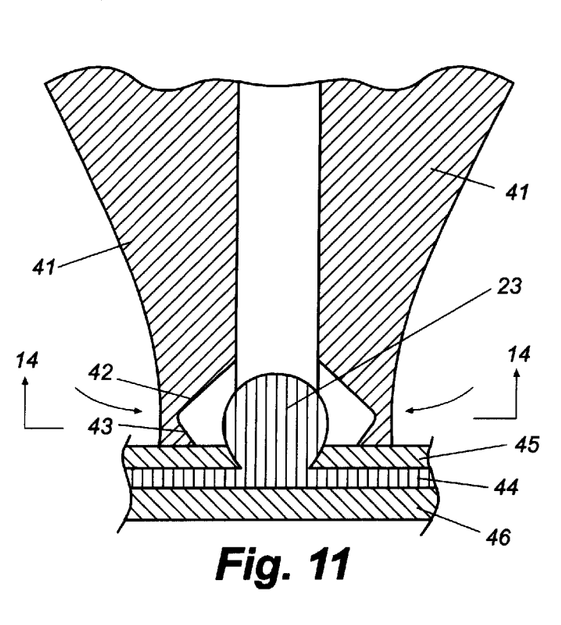
FIGS. 11–14 show a fourth embodiment, for use in testing substantially spherical bumps.
Figure 12:
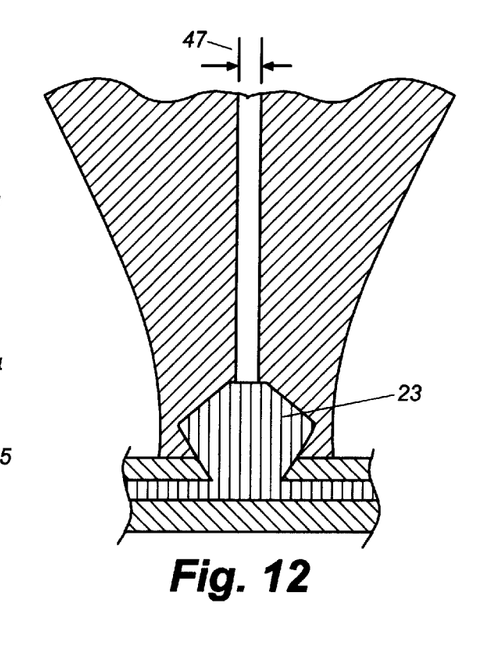
Figure 13:
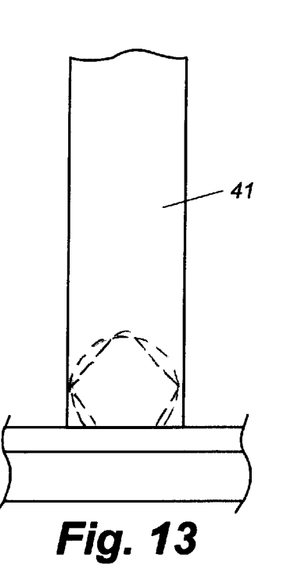

FIGS. 11–13 correspond to the views of FIGS. 8–10 and show a particularly preferred form of jaws for use with bumps which are substantially spherical.

Figure 14:
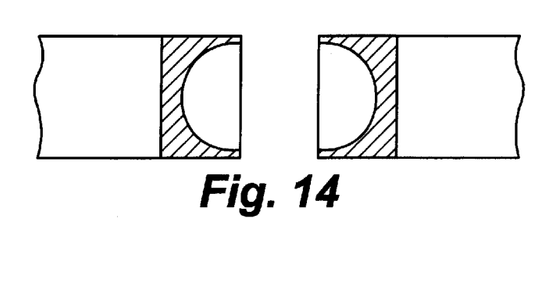

FIG. 11 shows the jaws in the open condition. Each jaw 41 is generally part circular in the plane perpendicular to the jaw axis (see the transverse cross-section of FIG. 14) and has an axial profile consisting of two single curvature surfaces 42,43 which lie approximately at right angles to one another, the meeting line of these conical surfaces (the plane of FIG. 14) being rounded to avoid a sharp transition. As is clearly illustrated in FIG. 11, the lower surface 43 is shorter than the upper surface 42 and thus does not extend closely to the jaw centre axis. The width of the lower surface 43 may be about 40% of the width of the upper surface 42.

The bump 23 illustrated in FIG. 11 is somewhat idealized and illustrated as a substantially spherical protrusion of an electrical track 44 lying between two layers of insulating material 45,46. In practice the bump is not likely to be exactly spherical though successive bumps are likely to be regular.

FIG. 12 illustrates the re-shaping of the bump which occurs as the jaws 41 are closed for test purposes, portions of the bump being deformed towards the apex and transverse diameter thereof. These deformed portions are in peripheral regions, and do not affect the bond of the bump which is to be tested in tension.

FIG. 13 shows a side elevation of the jaws, and illustrate the internal, rather angular jaw shape, and the idealized spherical shape of the bump. As in the previous embodiments it is intended that the jaws provide space for deformation of the bump (in order to increase contact area) yet do not place the bump under significant compressive stress. In this respect the separation distance 47 of the closed jaws (FIG. 12) may be adjustable to suit the bumps being tested, or may be under a feedback control to avoid excessive jaw loading. Such an arrangement provides a useful alternative in the case where non-contact areas of the jaw cannot be easily specified.

Solder is an easily deformed material; slight compression of the bump may cause extrusion between the closed jaws, and thus itself may increase the contact area of the jaw on the bump. Increased contact area has the consequence of reducing the average compressive surface load which is necessary to exert a predetermined tensile load, and is thus advantageous.

As illustrated in FIG. 12, the lower edge of the jaws 41 may slightly indent the bump. Whether this occurs in practice will depend on the precise shape of the bump to be tested. The indentation is slight, but capable of giving improved purchase on the bump. Since the bumps are usually regular, it is relatively straightforward to determine the degree of indentation and the degree of re-shaping which is permissible whilst avoiding shearing of the bump due to the re-shaping and indenting process.

Figure 15:
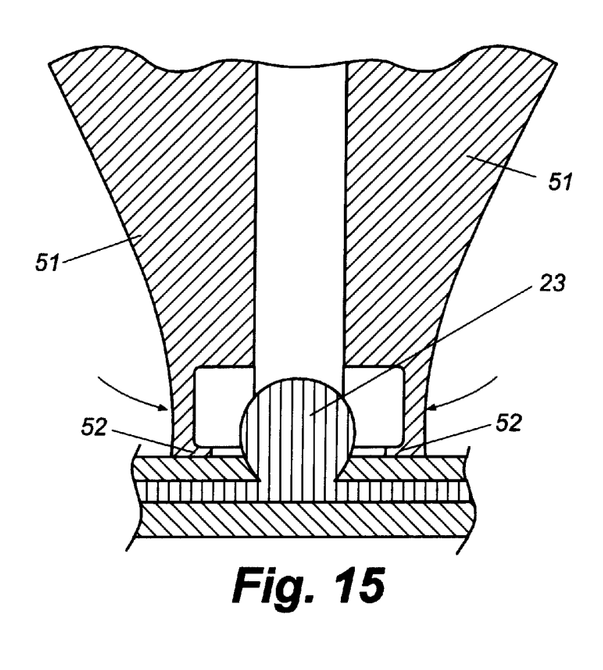
FIGS. 15–17 show a fifth embodiment for use in testing substantially spherical bumps.
Figure 16:
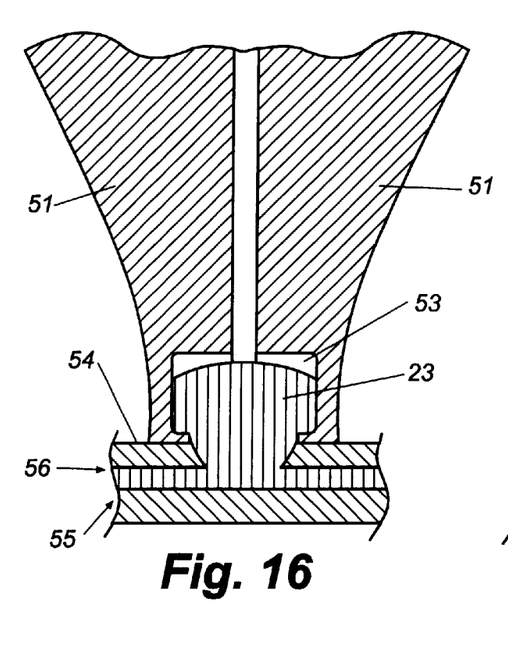
Figure 17:
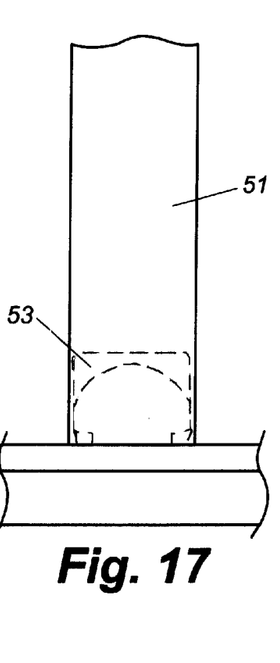

FIGS. 15–17 show another preferred embodiment useful for substantially spherical bumps. In this case the jaws 51 each have a narrow inwardly directed lip 52 which directly indents the bump 23 as illustrated in FIG. 16. The lips 52 are continuous and of substantially constant section so that they have a semi-circular shape when viewed from below. The jaw cavity 53 is drum-like and shaped to support the bump during the inevitable re-shaping, with the result that the bump is confined in a controlled manner around the entire periphery thereof.

It has been found that jaws of this shape are particularly effective, the indentation being insufficient to break the bump at the surface 54 of the substrate 55. Accordingly an accurate indication of the tensile breaking force at the level 56 of the bond interface can be determined. It will be noted from FIG. 15 that the lips 52 remain outside the diameter of the bump at the bond interface when in the closed condition, and the bump is supported around the entire periphery to prevent crushing.

Figure 18:
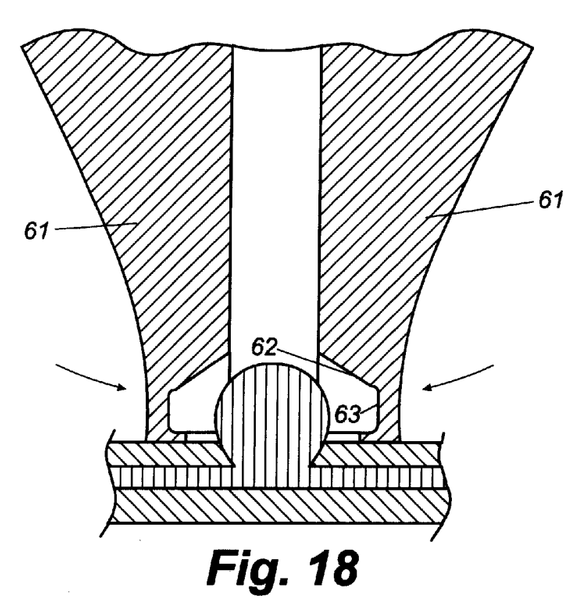
FIGS. 18–20 show a sixth embodiment, for use in testing substantially spherical bumps.
Figure 19:
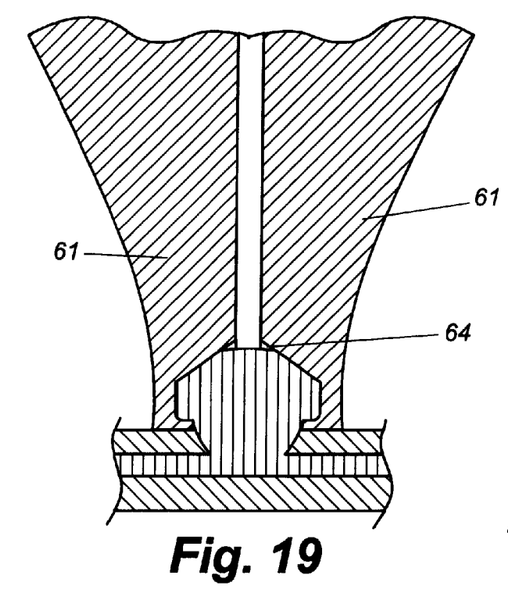
Figure 20:
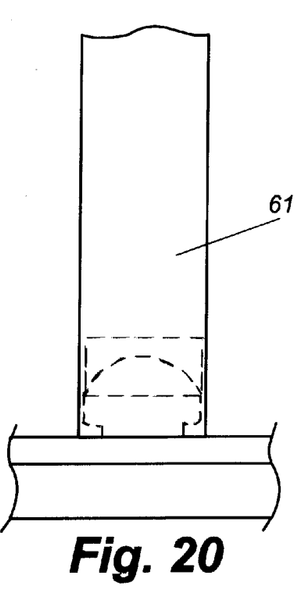

Another embodiment, similar to that of FIGS. 15–17, is illustrated in FIGS. 18–20. In this case the jaws 61 have a somewhat conical upper surface 62, and a lower area 23 of substantially constant diameter. Support of the re-shaped bump is substantially more complete so that the cavity 64 is small. The jaw lips 64 are substantially semi-circular as previously described.

Many other arrangements are of course possible within the scope of the invention described herein. Whilst the range of sizes of bumps is large, a typical component will have many bumps of the same size and type, for which a specific test head can be provided.

What is claimed is:

1. A method of tensile testing electrically conductive projections of an electrical device, the method comprising the steps of:

selecting a test head having closable jaws, the jaws defining a cavity corresponding closely to the shape and size of the projection to be tested, and having distal edge portions approaching the axis of the jaws;

clamping the projection in said jaws so that the jaws engage the projection over a substantial portion of the surface thereof; and applying a tensile load to the test head.

2. A test head of a device for tensile testing electrically conductive projections of an electrical device, said projections being approximately hemispherical, the test head comprising jaws having a center axis and movable from an open condition to a closed condition whereby said jaws close on a projection thereby to grip said projection and apply a tensile load thereto, wherein the jaws are arcuate, concave and adapted to closely engage the projection on a substantial part of the surface thereof, each jaw having a distal edge portion with an inwardly directed lower edge approaching the center axis of the jaws for engagement with a somewhat narrower neck portion of the projection.

3. A test head according to claim 2 wherein the jaws define a substantially spherical cavity.

4. A test head according to claim 2 wherein the jaws define a substantially cylindrical cavity.

5. A test head according to claim 2 wherein the jaws define a cavity that includes at least one substantial conical portion.

6. A test head according to claim 2 wherein said jaws are adapted to engage said projection over greater than 40% of the surface area of the projection.

7. A test head according to claim 6 wherein said jaws are adapted to engage said projection over greater than 75% of the surface area of the projection.

8. A test head according to claim 2 wherein said jaws define a relief volume to permit reshaping of said projection as said jaws close in use.

9. A test head according to claim 8 wherein said relief volume is less than 10% of the projection engaging surface of said jaws.

10. The method of claim 1 including the step of reshaping said projection as the jaws are closed, to conform the projection closely to the shape of the jaw cavity.

* * * * *